United States Patent [19]

Cavazza

[11] Patent Number: 5,747,536
[45] Date of Patent: May 5, 1998

[54] PHARMACEUTICAL COMPOSITION COMPRISING L-CARNITINE OR DERIVATIVE THEREOF AND TRIHYDROXY OR TETRAHYDROXYSTILBENE

[75] Inventor: Claudio Cavazza, Rome, Italy

[73] Assignee: Sigma-Tau Industrie Farmaceutiche Riunite S.p.A., Rome, Italy

[21] Appl. No.: 726,302

[22] Filed: Oct. 2, 1996

[30] Foreign Application Priority Data

Oct. 17, 1995 [IT] Italy ................ RM95A0687

[51] Int. Cl.$^6$ .................... A61K 31/205; A61K 31/05
[52] U.S. Cl. .................... 514/556; 514/733; 514/822; 514/824; 514/866
[58] Field of Search .................... 514/556, 733, 514/822, 824, 866

[56] References Cited

U.S. PATENT DOCUMENTS

| | | |
|---|---|---|
| 5,037,851 | 8/1991 | Cavazza . |
| 5,043,355 | 8/1991 | Cavazza . |
| 5,145,871 | 9/1992 | Cavazza . |
| 5,173,508 | 12/1992 | Cavazza . |
| 5,192,805 | 3/1993 | Cavazza . |
| 5,227,518 | 7/1993 | Cavazza . |
| 5,270,472 | 12/1993 | Taglialatela et al. . |
| 5,430,065 | 7/1995 | Cavazza . |
| 5,432,199 | 7/1995 | Cavazza . |
| 5,534,549 | 7/1996 | Tinti et al. . |
| 5,543,556 | 8/1996 | Tinti et al. . |
| 5,547,986 | 8/1996 | Tinti et al. . |

OTHER PUBLICATIONS

CA 120:153363, Bertelli et al., 1993.
CA 117:128195, Chung et al., 1992.
CA 123:275569, Bertelli et al., 1995.

*Primary Examiner*—Kimberly Jordan
*Attorney, Agent, or Firm*—Oblon, Spivak, McClelland, Maier & Neustadt, P.C.

[57] ABSTRACT

The coordinated therapeutic use of L-carnitine, lower alkanoyl L-carnitines or the pharmacologically acceptable salts thereof with resveratrol, resveratrol derivatives or resveratrol-containing natural products is disclosed for producing a medicament for the prophylaxis and treatment of cardiovascular disorders, peripheral vascular diseases and peripheral diabetic neuropathy.

20 Claims, No Drawings

PHARMACEUTICAL COMPOSITION COMPRISING L-CARNITINE OR DERIVATIVE THEREOF AND TRIHYDROXY OR TETRAHYDROXYSTILBENE

The present invention relates to a novel therapeutic use of L-carnitine, lower alkanoyl L-carnitine and their pharmacologically acceptable salts.

More specifically, the present invention relates to the co-ordinated use of L-carnitine, alkanoyl L-carnitines or their pharmacologically acceptable salts and a trihydroxy or tetrahydroxystilbene for the prophylaxis and treatment of cardiovascular diseases, peripheral vascular diseases and diabetic peripheral neuropathy.

Within the scope of the present invention, by "co-ordinated use" of the aforesaid compounds it is meant indifferently both the co-administration, i.e. the substantially concomitant supplementation of L-carnitine or alkanoyl L-carnitine or a pharmacologically acceptable salt thereof and a trihydroxy or tetrahydroxystilbene as active ingredients, and the administration of a combination preparation containing a mixture of the aforesaid active ingredients, in addition to suitable excipients, if any.

Consequently, the present invention also relates to orally, parenterally, rectally or transdermally administrable pharmaceutical compositions suitable for the treatment of cardiovascular disorders, peripheral vascular diseases and diabetic peripheral neuropathy, which comprises L-carnitine or a lower alkanoyl L-carnitine or a pharmaceutically acceptable salt thereof and a trihydroxy or tetrahydroxystilbene as active ingredients.

Among the trihydroxy and tetrahydroxystilbenes, resveratrol, 3,4',5-trihydroxystilbene, the derivatives thereof and the resveratrol-containing natural products, are particularly preferred.

Resveratrol and derivatives thereof are available as extracts or powders of natural products, mainly extracted from vitis vinifera and particularly from the skin, grapes, grape-seeds, grape-stalks and leaves of grapevine.

The alkanoyl L-carnitines useful for the novel therapeutic use of the present invention are those wherein the alkanoyl group, straight or branched, has 2 to 8, preferably 2 to 6, carbon atoms.

Particularly preferred are acetyl, propionyl, butyryl, valeryl and isovaleryl L-carnitine.

Pharmaceutically acceptable salts of L-carnitine or alkanoyl L-carnitine include, in addition to the inner salts, all pharmaceutically acceptable salts which are prepared by the addition of an acid to L-carnitine or alkanoyl L-carnitine, respectively, and which do not give rise to undesirable toxic or collateral effects. The formation of pharmaceutically acceptable acid addition salts is well known in the pharmaceutical technology.

Non-limiting examples of suitable salts include the chloride, bromide, orotate, acid aspartate, acid citrate, acid phosphate, acid fumarate, lactate, maleate and acid maleate, acid oxalate, acid sulphate, glucose phosphate, tartrate and acid tartrate.

For the sake of simplicity and clarity, hereinbelow reference will be made to L-carnitine and resveratrol and its derivatives only, it being understood, however, that whatever disclosed in connection with L-carnitine and resveratrol equally applies to the above-identified alkanoyl L-carnitines and the pharmacologically acceptable salts of both L-carnitine and the foregoing alkanoyl L-carnitines as well as to trihydroxy and tetrahydroxystilbenes, in general.

Previous therapeutic uses of L-carnitine are already known.

For instance, L-carnitine has been used in the cardiovascular field in the treatment of acute and chronic myocardial ischaemia, angina pectoris, cardiac arrhythmias and insufficiency. In nephrology, L-carnitine has been administered to chronic uraemic patients who are subject to regular haemodialysis treatment with a view to counteracting muscular asthenia and the onset of muscular cramps. Further therapeutic uses relate to the restoration to normal of unbalanced HDL/(LDL+VLDL) ratio and total parenteral nutrition. It is also known the use of L-carnitine for treating certain myopathies and muscular dystrophies.

Resveratrol, 3,4',5-trihydroxystilbene, belongs to the class of stilbenic phytoalexins which include various trihydroxy- and tetrahydroxystilbenes.

Resveratrol is the one present in largest amounts In red grapes and responsible for favourable pharmacological effects.

Data have recently been reported on the biological activity of resveratrol (Elliot G. R., Lanwen A. P. M., Bonta L. L., Agents Actions 32, 88, 1991: Ronca F., Palmieri L., Malengo S., Bertelli A., Int. J. Tiss. Reac. 16, 187, 1994; Amico Roxas M., Caruso A., Cutuli V. M. C., Bernardis E., INWIN ABS-Geneva 31-4-1993).

In popular medicine there was already an awareness that extracts from the roots of plants (*Polygonum cuspidatum* and *Polygonum multiflorum*) containing products such as resveratrol could be used in the prevention and therapy of atherosclerosis (Arichi H., Kimura Y., Okuda H., Baba K., Korawa Arichi S., Chem. Pharm. Bull., 30, 1766, 1982).

More recently, this activity of theirs has been found to be related mainly to resveratrol and its ability to inhibit cyclo-oxygeNases and lipo-oxygenases with a consequent reduction in the production of thromboxanes and leukotrienes which are known for their inflammatory and platelet aggregation action (Kimura Y., Okuda H., Arichi S., Biochem. Biophys. Acta 834, 275, 1985: Kimura Y., Okuda H., Arichi S., J. Med. Pharm. Soc. Watran-Yaku 2, 516, 1985) and to its antihyperoxidative ability (Kimura Y, Ohminami H., Okuda H., Baba K., Kozawa M., Arichi S., Plant. Med. J. Med. Plant Res. 49, 51, 1983).

Recent data in the literature indicate, moreover, that the onset of diabetic peripheral neuropathy is facilitated by increased platelet aggregation [(Medical treatment of diabetic arteriopathy) Got I., Ziegler O., Drouin P., J. Mal. Vasc. 18(1), 30–6, 1983; (Coagulation and fibrinolytic parameters in patients with various angiopathies-analysis in cerebral thrombosis, diabetic and vasculitic neuropathies) Kohriyama T., Katayama S., Tanaka E., Yamamura Y., Nakamura S., Rinsho-Shinkeigaku Jun. 33(6), 696–11, 1993: (Relationships between haemostatic factors and capillary morphology in human diabetic neuropathy) Ford I., Malik R.A., Newrick P. G., Preston F. E., Ward J. D., Greaves M., Thromb. Haemost, Dec. 7, 68(6), 628–33, 1992].

There has recently been an increase in interest in resveratrol as a result of epidemiological data showing a lower incidence of mortality due to cardiovascular damage even in populations with a high calorie consumption with a high percentage of lipids, but whose diets included red wine, as compared to populations who had a lower calorie consumption and lower percentage of lipids, but whose diets did not include wine, particularly red wine (Seigneur M., Bonnet Y., Dorian B., Beuchimal D., Dronillet F., Gouverneur G., Larrue Y., Crockett R., Bricaud H., J. Appl. Card. 5, 215, 1990; Siemann E. H., Creasy L. L., Am. J. Enol. Vitic. 43, 49, 1992; Renaud S., De Lorgeril M., Lancet 339, 1523, 1922; Scharp D., Lancet 341, 27, 1993).

Research conducted on the components present in red wine possibly responsible for this favourable effect has succeeded in identifying the presence in the wine of numerous products from grapes which are endowed with pharmacological properties, and particularly the presence of high percentages of resveratrol (Creasy L. L., Coffee L. L., J. Am. Soc. Hort. Sci. 113, 230, 1988: Ylandet P., Bessis R., Ganoixheron B., Am. J. Enol. Vitic. 42, 41, 1991).

Its isolation and then its synthesis have revealed that this phytoalexin effectively possesses many pharmacological activities which can be regarded as responsible for the protective effects of red wine at cardiovascular level (Frankel E. N., Kanner Y., Parks E., Kinsella Y. E., Lancet 341, 454, 1993).

In addition to its ability to modulate the synthesis of eicosanoids, resveratrol has proved capable of promoting the formation of nitroxides with a vasodilatory action and of inhibiting platelet aggregation induced by collagen or ADP (Fitzpatrick D., Steven L., Coffee R. G., Am. J. Physiol., 265 (Heart Circ. Physiol. 34, 774, 1993).

The resveratrol content of red wine is related to the type of grape the wine is produced from and the region where the grapes are grown (Mattivi F., Riv. Vitic. Enol. 1, 37, 1993).

Its presence, in differing percentages, can also be found both in the grape skins and in the pips or grape stalks (Langcake P., Pryce R., Experimentia 33, 151, 1977; Pezet R., Pont V., Plant Physiol. Biochem. 25, 603, 1988).

Its concentration is higher In grapes affected by a number of typical diseases of the vine and this has been attributed, amongst other things, to the antimould and antiparasite effect which resveratrol is capable of exerting and to an increase in its productive self-regulation in the presence of such diseases (Dercks W., Creasy L. L., Physiol. Molec. Plant Pathol. 34, 189, 1989; Langcake P., Physiol. Plant Pathol. 18, 213, 1981).

The invention described herein is based on the surprising synergic effect which occurs on combining carnitine or one of its derivatives and resveratrol or one of its derivatives, or natural compounds containing resveratrol.

The compositions according to the invention prove particularly effective in inhibiting platelet aggregation, vascular thrombo-embolic lesions and atherosclerosis and can thus be used in the pharmaceutical, dietetic and alimentary fields for the prevention or treatment of cardiovascular diseases, peripheral cardiopathies and diabetic peripheral neuropathies.

In such compositions the weight-to-weight ratio of resveratrol or its derivatives or extracts or powder of grapes containing resveratrol to L-carnitine or its derivatives ranges from 1:1 to 1:1000 and is preferably 1:500.

On the one hand, in fact, L-carnitine and particularly propionyl L-carnitine can act by varying the lipid substrate from which come, as a result of the action of cyclooxygenases and lipo-oxygenases, the various vasoconstricting and pro-aggregation factors, reducing their formation and facilitating the synthesis of antiaggregating and vasodilatory factors.

Resveratrol, on the other hand, can directly inhibit the action of the cyclo-oxygenase and lipo-oxygenase enzymes and the release of pro-inflammatory eicosanoids and leukotrienes and platelet aggregation promotors. To this we should add the antihyperoxidative effect common both to L-carnitine and to resveratrol and the ability of carnitine to inhibit the vasoconstricting and hypertensive action of endothelin, whereas resveratrol may be capable of releasing nitroxide which is known to exert a vasodilating action.

The routes of interaction between carnitine and resveratrol are therefore multiple and a combination of the two substances is useful for the purposes of preventing and treating pathological conditions related to cardiovascular disorders of the thrombo-embolic and atherosclerotic type and to diabetic peripheral neuropathy.

We shall now report the results of a number of tests which confirm the unexpected potent synergism between carnitine and resveratrol or extracts or powders from the skins, pips or stalks of grapes and containing high percentages of resveratrol.

Toxicology

The tests performed both in mice and in rats administering combinations of high doses both of L-carnitine or its derivatives and resveratrol or grape extracts (with a resveratrol concentration of approximately 0.1%) have demonstrated the low toxicity and good tolerability of the new composition. The administration of up to 1 g/kg of L-carnitine or its derivatives per os in the rat together with high doses of resveratrol (up to more than 0.5 g/kg) or grape extracts (up to more than 1 g/kg) revealed no toxic reactions worthy of note. Similarly well tolerated appeared to be protracted administration through the diet every day for three consecutive months with a combination of both L-carnitine and its derivatives together with resveratrol or grape extracts containing resveratrol. At the end of this treatment no abnormalities of any of the various biological parameters considered (weight gain, haematocrit, serum glucose, BUN, etc.) were detected, nor of the main organs examined at histology (liver, heart, lungs, adrenal glands, gonads).

Platelet Aggregation Tests

Platelet-rich plasma (PRP) was obtained from the blood of volunteers by centrifuging the plasma at 145 x g for 5 min at 22° C. The number of platelets was determined using a CA 580A (Delcon) Platelet Counter. The number of platelets was brought down to a fixed value of 300,000 platelets/ml by adding platelet-poor plasma (PPP). PPP was obtained by centrifuging blood at 1600 x g for 10 min at 22° C.

Platelet aggregation was determined photometrically (Born G.V.R., Nature 194, 927, 1962) using an Elvi 840 aggregometer in plastic test tubes under continual stirring at 1000 rpm. The maximum light transmission (100%) was measured with PPP readings, whereas 0% transmission was measured with PRP readings.

The degree of aggregation of PRP induced by the aggregating agent (collagen at 2.5 to 5 ng/ml) was calculated as a percentage of maximum transmission of light obtained with PPP using 250 1 PRP samples.

Aggregation was measured in basal conditions and after 10 minutes of incubation with L-carnitine, resveratrol, grape extract, and combinations of these preparations. Inhibition of the platelet aggregation induced by collagen (2.5 ng/ml) proved evident ($ED_{50}$ 3.5 ng/ml) for resveratrol and for grape extract ($ED_{50}$ with a resveratrol concentration equal to 2.5 ng/l), whereas for carnitine or its derivatives there was no significant change. However, when using a combination of the carnitines plus resveratrol at the same doses, 100% inhibition of platelet aggregation was achieved, thus showing a marked synergism between L-carnitine and resveratrol or grape extract containing resveratrol.

Tests with Experimental Atherosclerosis

A potentiation of the joint action of L-carnitine and resveratrol or grape extract has also been demonstrated in tests involving the induction of experimental atherosclerosis. The atherosclerotic vascular lesions induced according to the method described by M. R. Malinow (Atherosclerosis 48, 105, 1983) by adminstering an atherogenic diet (24% casein, 10% cotton oil, 5% salt, 60% sugar, 1% cholesterol, vitamin $D_2$ 200 m STU/g diet) to different groups of male Wistar rats for 6 consecutive weeks were reduced both by carnitine and by resveratrol, but the reductions were surprising when these products were administered in combination. With the administration of propionyl L-carnitine and resveratrol atherosclerotic lesions at the level of the aorta were completely inhibited, thus demonstrating an evident synergic effect of carnitine and resveratrol.

By way of examples and without in any way confining the possibilities to those listed, we give here a number of the possible formulations related to the invention described herein.

EXAMPLES

1) L-carnitine 500 mg, resveratrol 5 mg;
2) acetyl L-carnitine 500 mg, resveratrol 5 mg;
3) propionyl L-carnitine 500 mg, resveratrol 5 mg;
4) isovaleryl L-carnitine 500 mg, resveratrol 5 mg;
5) valeryl L-carnitine 500 mg, resveratrol 5 mg;
6) butryl L-carnitine 500 mg, resveratrol 5 mg;
7) L-carnitine 500 mg, lyophylized dry grape extract 250 mg (0.5% mg resveratrol titre);
8) acetyl L-carnitine 500 mg, lyophilized dry grape extract 250 mg (0.5% mg resveratrol titre);
9) propionyl L-carnitine 500 mg, lyophilized dry grape extract 250 mg (0.5% mg resveratrol titre);
10) isovaleryl L-carnitine 500 mg, lyophilized dry grape extract 250 mg (0.5% mg resveratrol titre);
11) L-carnitine 500 mg, resveratrol 10 mg;
12) L-carnitine 500 mg, lyophilized grape extract 250 mg (0.5% mg resveratrol titre), tocopherol acetate 20 mg, beta-carotene 10 mg.
13) L-carnitine 500 mg, resveratrol 5 mg, tocopherol acetate 20 mg, vitamin C 100 mg, selenium 40 mg.

I claim:

1. A pharmaceutical composition comprising (A) L-carnitine or alkanoyl L-carnitine wherein the alkanoyl group is straight or branched and contains 2–8 carbon atoms, or a pharmacologically acceptable salt thereof, and (B) a trihydroxy or tetrahydroxystilbene, as active ingredients; and a pharmacologically acceptable excipient therefor.

2. The composition of claim 1 wherein component (A) is an alkanoyl L-carnitine containing 2–6 carbon atoms.

3. The composition of claim 1 wherein component (A) is an alkanoyl L-carnitine wherein the alkanoyl group is selected from the group consisting of acetyl, propionyl, butyryl, valeryl and isovaleryl.

4. The composition of claim 3, wherein component (B) is resveratrol.

5. The composition of claim 1 wherein component (B) is 3,4',5-trihydroxystilbene or 3,4',5-trihydroxystilbene-3-beta-mono-D-glucoside, or a pharmacologically acceptable salt or ester thereof.

6. The composition of claim 1, wherein component (B) is resveratrol, extracted from *Vitis vinifera*.

7. The composition of claim 1 wherein component (B) is resveratrol.

8. A method of inhibiting platelet aggregation comprising administering to a patient in need thereof platelet aggregation inhibiting amounts of the composition of claim 7.

9. A method of inhibiting atherosclerotic lesions comprising administering to a patient in need thereof atherosclerotic lesion reducing amounts of the compositions of claim 7.

10. The method of claim 9 wherein component (A) is propionyl L-carnitine.

11. The composition of claim 1, wherein the weight ratio of (B):(A) is from 1:1 to 1:1,000.

12. The composition of claim 1, which additionally comprises one or more polyphenols, anthocyamins, anthocyanosides, vitamins, mineral salts, antioxidants and vegetable fibers.

13. The composition of claim 1, which is in the form of a powder, granule, lyposome, tablet, capsule or vial.

14. A method of inhibiting platelet aggregation comprising administering to a patient in need thereof platelet aggregation inhibiting amounts of the composition of claim 1.

15. The method of claim 14 wherein said administering is orally, parentally, rectally, or transdermally.

16. The method of claim 14, wherein said administering is carried out to treat a patient with diabetic peripheral neuropathy.

17. A method of inhibiting atherosclerotic lesions comprising administering to a patient in need thereof atherosclerotic lesion reducing amounts of the composition of claim 1.

18. The method of claim 17 wherein said administering is orally, parentally, rectally or transdermally.

19. The method of claim 17, wherein said administering is carried out to treat a patient with atherosclerosis.

20. A composition comprising (A) L-carnitine or an alkanoyl L-carnitine wherein the alkanoyl group is straight or branched and has 2–8 carbon atoms, or a pharmacologically acceptable salt thereof, and (B) a trihydroxy or tetrahydroxystilbene.

* * * * *